United States Patent
Ganin et al.

(10) Patent No.: US 6,459,765 B1
(45) Date of Patent: Oct. 1, 2002

(54) AUTOMATIC EXPOSURE CONTROL AND OPTIMIZATION IN DIGITAL X-RAY RADIOGRAPHY

(75) Inventors: Alexander Ganin, Whitefish Bay, WI (US); Ping Xue, Cottage Grove, WI (US); Kenneth S. Kump, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/752,847

(22) Filed: Dec. 28, 2000

(51) Int. Cl.[7] .................................................. H05G 1/44
(52) U.S. Cl. ........................ 378/108; 378/97; 378/98.7; 378/98.8
(58) Field of Search ..................... 378/97, 98.7, 98.8, 378/108

(56) References Cited

U.S. PATENT DOCUMENTS

| | | | |
|---|---|---|---|
| 4,996,413 A | | 2/1991 | McDaniel et al. ........ 250/208.1 |
| 5,008,915 A | * | 4/1991 | Vlasbloem ................... 378/108 |
| 5,751,783 A | | 5/1998 | Granfors et al. ............ 378/108 |
| 5,949,811 A | * | 9/1999 | Baba et al. .................. 378/108 |
| 6,018,565 A | * | 1/2000 | Ergun et al. ................... 378/95 |
| 6,047,042 A | * | 4/2000 | Khutoryansky et al. ...... 378/62 |
| 6,243,441 B1 | * | 6/2001 | Zur ............................. 378/98.8 |

* cited by examiner

*Primary Examiner*—David P. Porta
*Assistant Examiner*—Therese Barber
(74) *Attorney, Agent, or Firm*—McAndrews, Held & Malloy, Ltd.; Peter J. Vogel; Michael A. Dellapenna

(57) ABSTRACT

An automatic exposure control for an x-ray system using a large area solid state x-ray detector (26) includes an exposure control (36, 34) arranged to generate data of interest within the data generated by the detector and to adjust the dosage of x-rays to a predetermined level in response to data of interest so that an x-ray image of a patient is generated using the predetermined level.

32 Claims, 2 Drawing Sheets

AUTOMATIC EXPOSURE CONTROL AND OPTIMIZATION IN DIGITAL X-RAY RADIOGRAPHY

BACKGROUND OF THE INVENTION

The field of the invention is x-ray imaging systems, and particularly, automatic exposure control and exposure optimization for x-ray systems.

Automatic exposure control (AEC) is used in x-ray imaging equipment to control the exposure per image. The goal is to maintain image quality while minimizing patient exposure. The AEC develops a signal proportional to the x-ray flux into the image receptor. This signal is used to regulate the total exposure for each image either by terminating the exposure or by adjusting the x-ray flux rate. In this usage, the x-ray technique (kVp, spectral filter, focal spot, etc) is prescribed by the operator. Often these are preset and selected based on patient size and anatomy to be imaged. Thus, the role of the AEC is to regulate the correct total exposure.

There are several methods of automatic exposure control currently in use. One of these uses an ionization chamber detector placed between the patient and the imaging detector. The ion chamber detector can be composed of several separate chambers, in which case the exposure-control signal can come from any single chamber or a combination of chambers. One disadvantage of this type of detector is that some of the radiation that would otherwise contribute to signal in the image receptor is lost because of attenuation in the ion chamber. Such chambers must also be carefully constructed so that any variation in absorption over their area is small enough to preclude artifacts in the detected image.

In another AEC method an ion chamber is placed behind the image receptor. In this position it does not intercept x-rays used for imaging, but the available radiation, and thus the signal in the ion chamber, is reduced because of attenuation in the image receptor and any associated packaging or shielding. The thickness of the ion chamber could be increased to increase its sensitivity, but this would make the imaging system more bulky. Some AEC systems employ a scintillating screen coupled to a light sensor in place of the ion chamber.

Another AEC method, which is used with image intensifier based systems, collects some of the light from the image gate at the output of the image intensifier and detects the brightness level with a photosensor. A disadvantage of this AEC method is that the light-pickup device is placed in the image path. This can lead to interference of the image by the pickup device in some imaging situations.

X-ray imaging systems that employ a large area solid-state x-ray detector, such as that described in U.S. Pat. No. 4,996,413 entitled "Apparatus And Method For Reading Data from An Image Detector," cannot use the AEC method employed in image intensifier systems. Unlike an image intensifier system, there is no minified light image from which light can be conveniently collected. Also, one of the design objectives when using large area solid-state detectors is to reduce the bulk of the detector package. This makes the use of an ion chamber placed in front of or behind the image detector less desirable.

U.S. Pat. No. 5,751,783 describes automatic exposure control for an x-ray system using a large area solid state x-ray detector including an array of photodiodes located behind the x-ray image detector to measure photons passing there through. The resulting currents from selective ones of these photodiodes are combined to provide a signal used to control the x-ray exposure.

The x-ray technique is selected prior to patient imaging based on apriori knowledge of patient size and anatomical view. These technique tables are often provided by the equipment manufacturer and are often not optimized, nor ideal for a particular patient or anatomy. Other times the operator does not select the appropriate anatomical view or patient size being imaged. The result can be an image with poor image quality or the wrong patient exposure. An automatic means for x-ray technique optimization and exposure control is needed.

BRIEF SUMMARY OF THE INVENTION

The preferred embodiment is useful in an x-ray system for exposure control that generates an x-ray image of a patient while controlling the dose of x-rays received by a patient in order to generate the image. In such an environment, an apparatus embodiment comprises a source of x-rays and a digital detector arranged to generate detector data in response to the x-rays. An exposure control is arranged to generate data of interest within the detector data and to adjust the technique and/or dosage of x-rays to a predetermined level in response to the data of interest so that the image is generated to a predetermined image quality standard.

A comparable method also is included in another embodiment. By using the foregoing techniques, the image quality can be increased while the patient x-ray dose is controlled. In addition, system cost is reduced by eliminating the need for an ion chamber and system calibration time and operator errors also are reduced. The techniques provide an AEC signal without producing image artifacts or significantly increasing the total acquisition time or significantly increasing patient x-ray dose.

DETAILED DESCRIPTION OF THE INVENTION

Figure 1:
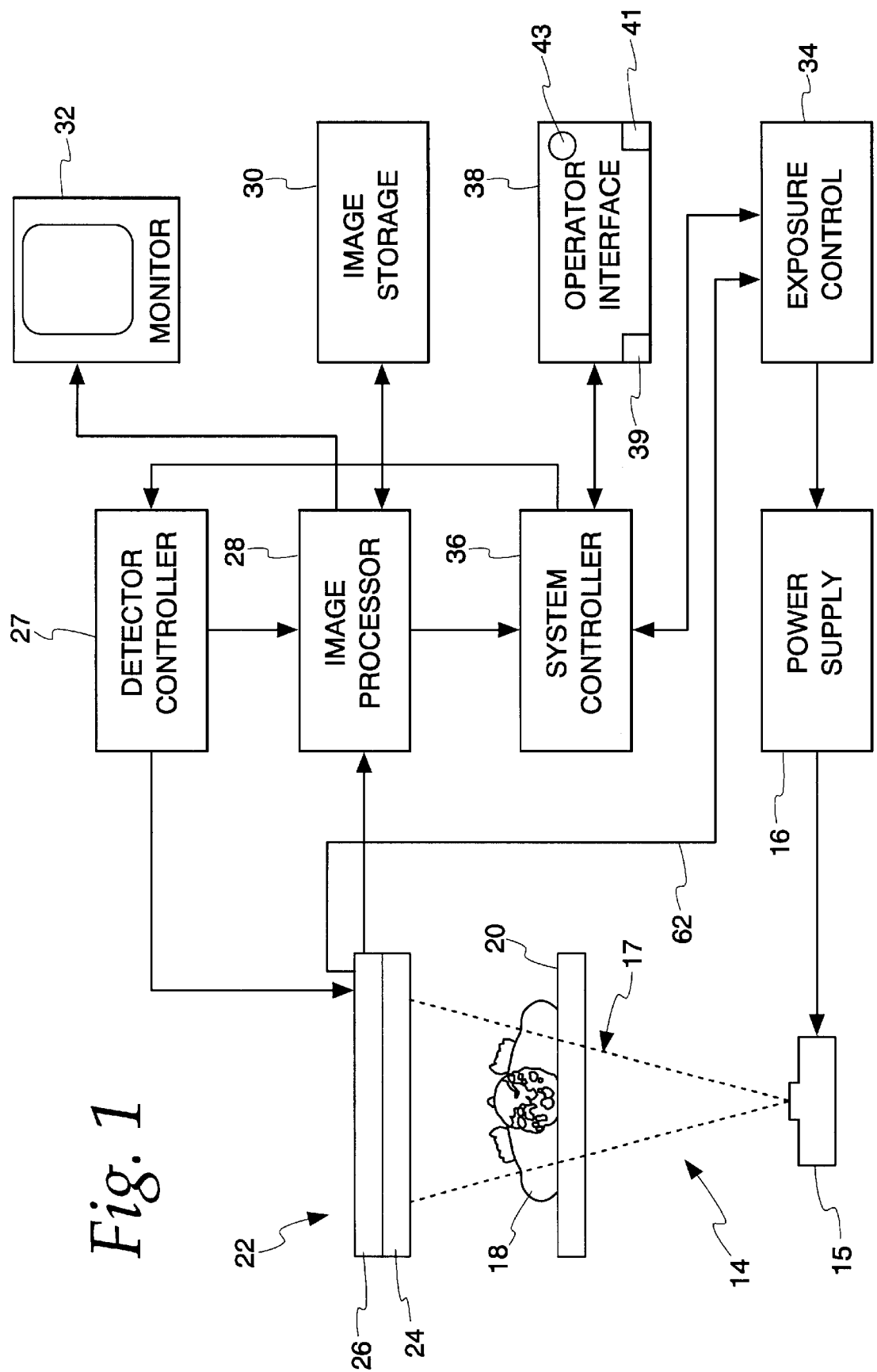
FIG. 1 is a schematic block diagram of a preferred form of x-ray system employing a preferred embodiment of the invention.

With initial reference to FIG. 1, an x-ray system 14 includes an x-ray tube 15 which, when excited by a power supply 16, emits an x-ray beam 17. As illustrated, the x-ray beam is directed toward a patient 18 lying on an x-ray transmitting table 20. The portion of the beam, which is transmitted through the table and the patient, impinges upon an x-ray detector assembly 22. The x-ray detector assembly 22 comprises a scintillator 24 that converts the x-ray photons to lower energy photons in the visible spectrum. Contiguous with the scintillator 24 is an image photo detector array 26, which converts the light photons into an electrical signal. A detector controller 27 contains electronics for operating the detector array 26 to acquire an image and to read out the signal from each photo detector element.

The output signal from the image photo detector array 26 is coupled to an image processor 28 that includes circuitry for collecting, processing and enhancing the x-ray image signal. The processed image is displayed on a video monitor 32 and may be stored in an image storage device 30. A system and image detector controller 36, which receives commands from the user via an operator interface panel 38, including a prep switch 39 and an exposure switch 41, governs the overall operation of the x-ray apparatus 14. A light 43 is illuminated during various modes of operation as will be described later.

The image photo detector array 26 consists of amorphous silicon devices on a glass substrate. A portion of the light from the scintillator 24 is transmitted through these silicon devices and through the spaces between them. In addition, some of the x-rays are transmitted through both the scintillator 24 and the image photo detector array 26. The output signal from array 26 also is coupled to an exposure control circuit 34.

In general, the preferred embodiment utilizes a Preshot image from digital detector 26. The Preshot image is obtained from a small dose of x-rays occurring before the x-ray exposure that results in an image of a patient. The number, location and size of the regions of interest (ROIs) on the Preshot image, are used for exposure control, and are defined based on a prescribed Anatomy/View or are automatically calculated from the image data created in detector 26. A typical anatomy view is a chest view. Thus, the AEC "field of view", can be adjusted for different imaging procedures by selectively combining the signal from one or more ROIs of desired shape and size.

Different image based algorithms can be used to derive the appropriate ROIs. The simplest approach is to create the ROIs that have the same size and shape as the Ion Chamber cells (although no ion chamber is used in the preferred embodiment). In this case, the mean x-ray signals in the selected ion chambers are calculated. The x-ray detector is calibrated such that image gray values can be converted to exposure level through a conversion factor transfer function.

Exposure(mR)=F1(gray_level)

For our detector, this function is linear, however, the slope and intercept depend upon the x-ray energy spectrum.

To calculate the mAs required of the full-dose shot, we scale the preshot mAs by the measured mean gray value in the preshot image and the desired exposure level in converted gray values:

Required mAs=preshot_mAs*F1 (desired_exposure)/preshot_ROI_gray_level    (1)

Consider the case where a preshot with mAs (milli-amp-seconds) of 0.1 is used with a given kvp, focal spot size, mA, etc, and the desired detected exposure level is 3.4 micro R. The system has been calibrated such that the conversion factor is known to be 300 counts/micro_R. The mean value has been calculated in the ROI representing the location of the ion chambers to be 50 counts. Thus, using equation (1), we calculate:

Required mAs=0.1*(300*3.4)/50=2.04

The exposure controller now commands the system to operate at the required_mAs.

After Prep. Switch 39 is pressed, the system defines the Preshot parameters based on the following parameters prescribed by a user of the system: Anatomy/View, Customer Dose selection and Patient size. Patient size generally is limited to small, medium or large. The user enters the parameters from operator interface 38. The Preshot parameters include the x-ray exposure technique, the detector timing, and the synchronization between these two. The x-ray exposure technique includes KV, ma, Mas and many other parameters known to x-ray technicians. The detector timing includes offset timing and readout time. Through interface 38, a user enters all of the Preshot parameters.

After Expose switch 41 is pressed, the system performs the following steps

Generating an Offset image;

Acquiring a Preshot image;

Calculation of optimal x-ray dosage, for example, by adjusting exposure time; and Generating an exposure or Final image based on calculated optimal x-ray dosage.

The system calculates exposure time based on a required signal to noise ratio (SNR) by performing the following steps:

Storing the required $SNR_{req}$ value for a particular Anatomy/View;

Measuring $SNR_{meas}$ on Preshot image inside predefined (or calculated) ROIs;

Calculating the ratio $SNR_{req}/SNR_{meas}=K$, $SNR \sim \sqrt{T}$; and

Calculating $T_{exp}=K^2 \times T_{preshot}$.

The foregoing terms have the following meanings: SNR is the signal to noise ratio, K is the predefined ratio of final exposure to the preshot exposure, and T is the exposure time of the x-ray pulse.

The Preshot image may be acquired in reduced matrix size (e.g. 128×128 pixels) for the same field of view (FOV) in order to minimize the extra time. A full matrix size may be, for example, 2,000×2,000 pixels.

For example, the preshot x-ray technique is defined as the predetermined kVp with exposure time to "fit" within the preshot expose window (<10 msec (milliseconds)) and the mA to deliver the requested exposure (5–10% of a "normal" dose used to generate a diagnostic image of a patient). In other words, the x-ray dosage during the normal exposure is 10 to 50 times greater than the x-ray dosage during the pre-exposure preshot step. The predetermined kVp typically may vary, for example, from 40 to 150 kVp. The Preshot exposure window varies as needed up to about 10 milliseconds depending on the selected anatomy of the patient and the selected view. The Preshot function adds about 20 ms to total acquisition time.

In one simple embodiment, the Preshot analysis simply calculates image statistics on rectangular regions of interest that mimic the current ion chamber positions (although no ion chamber is used in the preferred embodiment). The final image technique may be calculated to achieve a particular mean target signal level (or target dose) or to attain a particular signal to noise ratio. More sophisticated algorithms may analyze the image to locate particular anatomical features. For example, the image may be segmented using thresholding or analysis to identify the regions of interest to perform statistical analysis. A preferred segmentation method utilizes a mixture of spatial and statistical algorithms. The collimator and raw radiation areas are removed using morphological operations, such as dilation and erosion operations with pre-selected kernel sizes and/or. Next, the anatomical contents are delineated using a gradient filter that identifies boundaries. With a gradient image, the edges or object boundaries are assigned a high absolute value, and flat areas are assigned a value of 0. An edge-strength threshold is calculated based upon the x-ray system patient input dose and the expected (heuristic) values based upon the patient anatomy. For example, an image threshold may be calculated based on an estimate of noise in the image (such as by using standard deviation in a flat region) divided by the patient input dose times a scalar that depends upon the anatomy. The output is a set of non-rectangular regions of interest, presumably from different anatomical features. The image is now segmented. Another such algorithm is described in U.S. application Ser. No. 09/344,190, filed Jun. 24, 1999, in the name of Kenneth S. Kump, assigned to General Electric Company, and incorporated by reference in its entirety. The outputs of the segmentation algorithm are multiple regions of interest (ROIs) for different anatomical areas. Certain ROIs are selected based on a set of predefined rules using the size, shape, and gray level statistics such as min, mean, max, and standard deviation. In segmentation, the system focuses on the area surrounding the anatomy of interest, and the rest of the image may be ignored. As an example, the throat/larynx and spine form a patient segment of interest for a neck image acquisition. The system focuses on the segment of the medical diagnostic image comprising the throat, larynx, and spine in analyzing a neck image. As an example, the lungs and diaphragm form a segment of interest in a patient image for a chest image acquisition. The segment of the medical diagnostic image comprising the lungs and diaphragm is identified and the segment of interest for a chest image acquisition. The anatomy of interest is analyzed to identify at least one of a set of anatomy image characteristics, such as patient thickness.

The characteristics may be used to characterize the anatomical segments of interest. The anatomical segments of interest may be characterized in terms of patient parameters, such as the attenuation of the segments. Patient parameters may also include the brightest and darkest regions of the anatomy of interest. The analysis may also include correlating current data with a normalized patient and/or using a mathematical model of the anatomy of interest to characterize parameters.

The optimal exposure for the final image may be at the same Preshot x-ray spectrum (kVp and spectral filter), but at a calculated mAs (mA and exposure time calculation chosen to minimize patient motion and maximize tube life). Alternatively, the Preshot analysis may change the x-ray spectrum based on predefined technique charts or calculated based on estimated patient thickness and anatomy/view. These image acquisition parameters or settings are used to adjust the x-ray acquisition techniques visualization, and/or clarity of the anatomy and pathology of interest, while minimizing dose. For example, the kVp (x-ray energy, kilo-volt energy of x-ray beam) and spectral filters may be selected to optimize the bone/soft tissue separation at the segment of interest. The mAs (milliamps times seconds) and x-ray detector gain may be chosen to minimize target dose while maintaining a sufficient signal in the most dense area of the segment of interest.

A more complex algorithm could be implemented, which will calculate new kVp, MAs, filter and exposure time values. Features in an x-ray image generally comprise a map of a line integral of x-ray attenuations along the path of x-ray energy. In a preferred embodiment, the x-ray input may be determined via feedback from an x-ray source. The detected x-ray output may be measured once the x-rays have penetrated the patient. The equivalent patient thickness (in 2D) may be calculated for every pixel detected in the image. $I=I_o\exp(-u*x)$, where $I_o$ is incident x-ray exposure, u is an attenuation coefficient, x is patient thickness, and I is output x-ray exposure. In a preferred embodiment, an attenuation coefficient is assumed that matches the "average" tissue, for example, water. By rearranging the equation, x may be calculated. A map of patient thickness may be calculated using $x=-\ln(I/I_o)/u*$, where $u*$ is the assumed attenuation coefficient.

In order to normalize patient data, "median" patient attenuation maps may be developed for areas of interest (chest, abdomen, pelvis, etc.). Preferably, the "median" patient attenuation maps represent the $50^{th}$ percentile of people. In an exposure, the acquired patient map is compared to a corresponding median map for the area of interest. In a preferred embodiment, comparison of the maps is done by simple division. Numerical results greater than 1.0 indicate the patient anatomy is thicker than the median value. Numerical results less than 1.0 indicate the patient anatomy is thinner than the median value. Comparison of the maps may also be accomplished by segmenting the image into regions and dividing image region statistics. For example, a chest image may be segmented into a right lung region, left lung region, diaphragm region, neck region, head region, spine region, and, perhaps, background. The mean thickness in each region may be computed. Each region's mean thickness may be divided by the "median patient" data.

For a mathematical model of an anatomy, a two-dimensional mathematical equation is computed and the parameters of the resulting mathematical model are fit to the new patient thickness data. An example of a mathematical model includes a 2D polynomial. In a preferred embodiment, N normalized values are stored for the anatomical region of interest. Preferably, the patient image is segmented and normalized anatomical region of interest thickness values are computed.

For characterization of the segmented image, the normalized thickness data may be input into an equation or look up table to calculate kVp (kilo-volts, x-ray beam voltage) and mAs (milliamps times seconds, x-ray beam current). Preferably, the look up table comprises a pre-defined range of input thicknesses and imaging technique values. In a preferred embodiment, the look up table values are obtained using x-ray calibration phantoms and clinical trials designed to adjust the contrast-to-noise ratio per patient dose. Alternatively, an equation may be used to calculate the desired values. For example, kVp=A#P, where A is a 1xN adjustment matrix and P is a Nx1 model parameter matrix. Alternatively, P may be a Nx1 matrix of thickness values for anatomical regions of interest taken from the normalized thickness values. From mAs, mA (milliamps) and an image focal spot may be calculated. In a preferred embodiment, mA is calculated to minimize exposure time. Minimizing exposure time also minimizes patient motion. The smallest focal spot is chosen to minimize blur in the focal spot. However, a larger mA typically produces a bigger focal spot.

Figure 2:
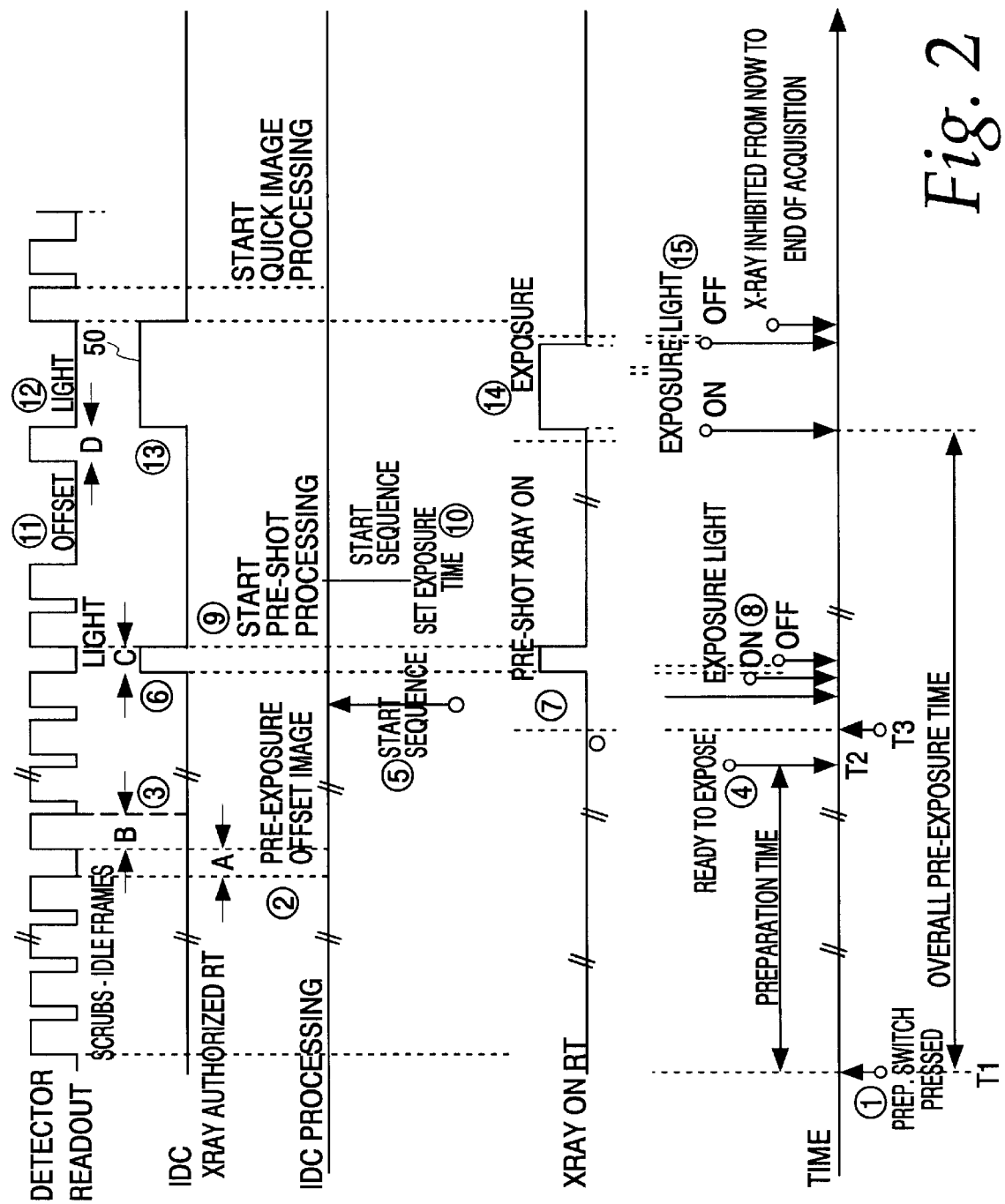
FIG. 2 is timing diagram illustrating one mode of operation of the system shown in FIG. 1.

Referring to FIG. 2, operation according to the preferred embodiment begins in step 1 at time T1 with the pressing of prep switch 39 (FIG. 1). As shown in the first line of FIG. 2, scrubs-idle frames are continuously generated by a clock in controller 36 in order to provide timing signals. In step 2, during time interval A, a dark offset image is generated in detector 26 due to background radiation. In step 3, during time interval B, the dark offset image is read by processor 28 and controller 36. In step 4, at time T2, the preparation time is completed, and the system is ready to generate the Pre-shot sequence of steps.

In step 5, shortly after time T3, controller 36 generates a start sequence command. In steps 6 and 7, during time C, controller 36 causes exposure control 34 and power supply 16 to generate a pre-exposure dose of x-rays which pass through patient 18 and which generate in detector 26 a pre-exposure image that results in pre-exposure data. The data is conditioned in a well-known manner by the pre-exposure offset value obtained by reading the dark image during time interval B. In step 8, light 43 is illuminated during time interval C.

In step 9, controller 36 begins pre-shot processing according to one or more of the previously described algorithms. In step 10, controller 36 sets the desired x-ray dosage by determining the proper x-ray exposure time based on the data acquired during time period C and execution of the algorithms.

In step 11, a dark offset image again is generated in detector 26 due to background radiation. In step 12, during time interval D, the dark offset image is read by processor 28 and controller 36.

In step 13, controller 36 generates an exposure x-ray authorization signal 50, and in step 14, controller 36 causes exposure control 34 and power supply 16 to generate an exposure dosage of x-rays that pass through patient 18 and generate a diagnostic image and data in detector 26. In step 15, during the generation of signal 50, light 43 is illuminated.

Those skilled in the art will recognize that the preferred embodiments may be altered and modified without departing from the true spirit and scope of the invention as defined in the accompanying claims.

What is claimed is:

1. In an X-ray system, apparatus for generating an X-ray image of a patient while controlling the dose of X-rays received by said patient in order to generate said image, said apparatus comprising:
    a source of X-rays;
    a digital detector to generate digital detector data in response to said X-rays; and
    an exposure control module to extract data of interest from said digital detector data and to generate a ratio of signal-to-noise ratios (SNR's) in response to, in part, said data of interest, and said exposure control module adjusting an X-ray dosage level in response to said ratio of SNR's.

2. The apparatus of claim 1 wherein said ratio of SNR's is generated from a required SNR and a measured SNR, wherein said measured SNR is generated in response to said data of interest, and said required SNR is pre-determined for a selected anatomy/view and is stored in said exposure control module.

3. The apparatus of claim 1 wherein said X-ray dosage level is adjusted by adjusting an exposure time.

4. The apparatus of claim 1 wherein said X-ray dosage level is adjusted by adjusting a current of said source of X-rays and an exposure time.

5. The apparatus of claim 1 wherein a voltage level of said source of X-rays is pre-determined for a selected anatomy/view and is applied to said source of X-rays when said anatomy/view is selected.

6. The apparatus of claim 1 wherein said exposure control module generates said data of interest by segmenting said digital detector data.

7. The apparatus of claim 1 wherein said exposure control module is arranged to segment said digital detector data by thresholding analysis.

8. The apparatus of claim 1 wherein said exposure control module is arranged to segment said digital detector data by histogram analysis.

9. The apparatus of claim 1 wherein said exposure control module is arranged to locate anatomical features of said patient in said digital detector data.

10. The apparatus of claim 1 further comprising a system control module programmed to cause said exposure control module to generate a first dose of X-rays resulting in first digital detector data, to adjust the dosage of X-rays to a predetermined level in response to said first digital detector data, and to generate a second dose of X-rays at said predetermined level to generate said image of said patient.

11. The apparatus of claim 10 wherein said second dose of X-rays is 10 to 50 times greater than said first dose of X-rays.

12. The apparatus of claim 10 wherein said system control module is programmed to cause said exposure control module to generate said first dose of X-rays in 10 milliseconds or less.

13. The apparatus of claim 1 wherein said exposure control module generates said data of interest by applying spatial and statistical algorithms to said digital detector data to generate one or more segmented regions of interest.

14. The apparatus of claim 13 wherein said exposure control module analyzes said one or more segmented regions of interest to measure one or more signal-to-noise ratios.

15. The apparatus of claim 14 wherein said exposure control module uses, at least indirectly, said one or more signal-to-noise ratios to access a lookup table or equation that results in said adjusting said X-ray dosage level.

16. The apparatus of claim 14 wherein said one or more signal-to-noise ratios are related to patient thickness.

17. In an X-ray system, a method for generating an X-ray image of a patient while controlling the dose of X-rays received by said patient in order to generate an image, said method comprising:
    generating a first dose of X-rays such that at least a portion of said first dose of X-rays pass through said patient;
    generating digital detector data in response to said first dose of X-rays;
    generating a ratio of signal-to-noise ratios (SNR's) in response to, in part, at least a subset of said digital detector data; and
    adjusting an X-ray dosage level in response to said ratio of SNR's to generate a second dose of X-rays.

18. The method of claim 17 wherein said generating said ratio of SNR's comprises using a required SNR and a measured SNR, wherein said measured SNR is generated in response to at least a subset of said digital detector data.

19. The method of claim 18 further comprising storing said required SNR such that said required SNR may be accessed when generating said ratio of SNR's, and wherein said required SNR is predetermined for a selected anatomy/view.

20. The method of claim 17 wherein said adjusting said X-ray dosage level is performed by adjusting an exposure time.

21. The method of claim 17 wherein said adjusting said X-ray dosage level is performed by adjusting a current of an X-ray source and an exposure time.

22. The method of claim 17 further comprising applying a voltage level to an X-ray source when a particular anatomy/view is selected, and wherein said voltage level is predetermined for said particular anatomy/view and is stored such that said voltage level may be accessed when generating said image.

23. The method of claim 17 further comprising segmenting said digital detector data to generate data of interest.

24. The method of claim 23 wherein said segmenting comprises applying thresholding analysis.

25. The method of claim 23 wherein said segmenting comprises applying histogram analysis.

26. The method of claim 23 wherein generating said data of interest comprises locating anatomical features of said patient in said digital detector data.

27. The method of claim 23 wherein generating said data of interest comprises analyzing said digital detector data with spatial and statistical algorithms to generate one or more segmented regions of interest.

28. The method of claim 27 further comprising analyzing said one or more segmented regions of interest to measure one or more signal-to-noise ratios.

29. The method of claim 28 wherein said one or more signal-to-noise ratios are used to access a lookup table or equation that results in said adjusting said X-ray dosage level.

30. The method of claim 28 wherein said one or more signal-to-noise ratios are related to patient thickness.

31. The method of claim 17 wherein said second dose of X-rays is 10 to 50 times greater than said first dose of X-rays.

32. The method of claim 17 wherein said generating said first dose of X-rays comprises generating said first dose of X-rays in 10 milliseconds or less.

* * * * *